US012784207B2

(12) United States Patent
Gurcan et al.

(10) Patent No.: US 12,784,207 B2
(45) Date of Patent: Nov. 3, 2026

(54) CREATING A TUMOR BUD GROUND TRUTH OF H AND E STAINED SLIDES AND AUTOMATED IDENTIFICATION OF TUMOR BUDS USING AN H AND E STAINED SLIDES

(71) Applicants: OHIO STATE INNOVATION FOUNDATION, Columbus, OH (US); WAKE FOREST UNIVERSITY HEALTH SCIENCES, Winston-Salem, NC (US)

(72) Inventors: Metin N. Gurcan, Winston-Salem, NC (US); Wendy L. Frankel, Hilliard, OH (US); Wei Chen, Worthington, OH (US); Muhammad Khalid Khan Niazi, Winston-Salem, NC (US)

(73) Assignees: OHIO STATE INNOVATION FOUNDATION, Columbus, OH (US); WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 210 days.

(21) Appl. No.: 18/730,593

(22) PCT Filed: Jan. 20, 2023

(86) PCT No.: PCT/US2023/060973
§ 371 (c)(1),
(2) Date: Jul. 19, 2024

(87) PCT Pub. No.: WO2023/141556
PCT Pub. Date: Jul. 27, 2023

(65) Prior Publication Data

US 2025/0166174 A1 May 22, 2025

Related U.S. Application Data

(60) Provisional application No. 63/301,353, filed on Jan. 20, 2022.

(51) Int. Cl.
*G06T 7/00* (2017.01)
*G16H 30/40* (2018.01)
*G16H 50/20* (2018.01)

(52) U.S. Cl.
CPC .......... *G06T 7/0012* (2013.01); *G16H 30/40* (2018.01); *G16H 50/20* (2018.01);
(Continued)

(58) Field of Classification Search
None
See application file for complete search history.

(56) References Cited

U.S. PATENT DOCUMENTS 10,957,041 B2 * 3/2021 Yip .......................... G06T 1/20
2019/0206055 A1 7/2019 Gurcan et al.
(Continued)

OTHER PUBLICATIONS

International Searching Authority (ISA/US). International Search Report and Written Opinion. Issued in PCT/US2023/060973 on May 2, 2023. 14 pages.
(Continued)

*Primary Examiner* — Chikaodili E Anyikire
(74) *Attorney, Agent, or Firm* — Meunier Carlin & Curfman LLC

(57) ABSTRACT

Tumor budding (TB) is defined as a cluster of one to four tumor cells at the tumor invasive front. Though promising as a prognostic factor for colorectal cancer, its routine clinical use is hampered by high inter-and intra-observer disagreement on routine H&E staining. Therefore, automated methods are provided that minimize the inter-and intra-observer disagreement for tumor bud detection on images of H&E-stained tissue sections.

17 Claims, 8 Drawing Sheets

(52) U.S. Cl.
CPC ............... *G06T 2207/10056* (2013.01); *G06T 2207/20036* (2013.01); *G06T 2207/20081* (2013.01); *G06T 2207/20084* (2013.01); *G06T 2207/30024* (2013.01); *G06T 2207/30096* (2013.01)

(56) References Cited

U.S. PATENT DOCUMENTS

| | | | | |
|---|---|---|---|---|
| 2019/0295252 | A1* | 9/2019 | Fuchs ................ | G06V 10/7635 |
| 2020/0302608 | A1 | 9/2020 | Kaffenberger et al. | |
| 2021/0256690 | A1 | 8/2021 | Yip et al. | |
| 2023/0162515 | A1* | 5/2023 | Kozlowski ........... | G06V 20/695 382/133 |

OTHER PUBLICATIONS

M. Boxberg, M. Jesinghaus, C. Dorfner, C. Mogler, E. Drecoll, A. Warth, et al., "Tumour budding activity and cell nest size determine patient outcome in oral squamous cell carcinoma: proposal for an adjusted grading system," Histopathology, vol. 70, pp. 1125-1137, 2017.

P. V. Angadi, P. V. Patil, K. Hallikeri, M. Mallapur, S. Hallikerimath, and A. D. Kale, "Tumor budding is an independent prognostic factor for prediction of lymph node metastasis in oral squamous cell carcinoma," International journal of surgical pathology, vol. 23, pp. 102-110, 2015.

X. Li, B. Wei, C. Sonmez, Z. Li, and L. Peng, "High tumor budding count is associated with adverse clinicopathologic features and poor prognosis in breast carcinoma," Human Pathology, 2017.

M. Jesinghaus, M. Boxberg, B. Konukiewitz, J. Slotta-Huspenina, A. M. Schlitter, K. Steiger, et al., "A Novel Grading System Based on Tumor Budding and Cell Nest Size Is a Strong Predictor of Patient Outcome in Esophageal Squamous Cell Carcinoma," The American Journal of Surgical Pathology, vol. 41, pp. 1112-1120, 2017.

K. Che, Y. Zhao, X. Qu, Z. Pang, Y. Ni, T. Zhang, et al., "Prognostic significance of tumor budding and single cell invasion in gastric adenocarcinoma," OncoTargets and therapy, vol. 10, p. 1039, 2017.

S. Olsen, J. Linda, R. C. Fields, Y. Yan, and I. Nalbantoglu, "Tumor Budding in Intestinal Type Gastric Adenocarcinoma is Associated with Nodal Metastasis and Recurrence," Human Pathology, 2017.

B. Huang, J. Cai, X. Xu, S. Guo, and Z. Wang, "High-Grade Tumor Budding Stratifies Early-Stage Cervical Cancer with Recurrence Risk," PloS one, vol. 11, p. e0166311, 2016.

N. Satabongkoch, S. Khunamornpong, T. Pongsuvareeyakul, J. Settakorn, K. Sukpan, A. Soongkhaw, et al., "Prognostic Value of Tumor Budding in Early-Stage Cervical Adenocarcinomas," Asian Pacific journal of cancer prevention: APJCP, vol. 18, p. 1717, 2017.

Y. H. Lai, L. C. Wu, P. S. Li, W. H. Wu, S. B. Yang, P. Xia, et al., "Tumour budding is a reproducible index for risk stratification of patients with stage II colon cancer," Colorectal Disease, vol. 16, pp. 259-264, 2014.

A. Mezheyeuski, I. Hrynchyk, M. Karlberg, A. Portyanko, L. Egevad, P. Ragnhammar, et al., "Image analysis-derived metrics of histomorphological complexity predicts prognosis and treatment response in stage II-III colon cancer," Scientific reports, vol. 6, p. 36149, 2016.

I. Zlobec, M. Hädrich, H. Dawson, V. Koelzer, M. Borner, M. Mallaev, et al., "Intratumoural budding (ITB) in preoperative biopsies predicts the presence of lymph node and distant metastases in colon and rectal cancer patients," British journal of cancer, vol. 110, p. 1008, 2014.

R. Cappellesso, C. Luchini, N. Veronese, M. L. Mele, E. Rosa-Rizzotto, E. Guido, et al., "Tumor Budding as a Risk Factor for Nodal Metastasis in Pt1 Colorectal Cancers: A Meta-Analysis," Human Pathology, 2017.

R. P. Graham, R. A. Vierkant, L. S. Tillmans, A. H. Wang, P. W. Laird, D. J. Weisenberger, et al., "Tumor Budding in Colorectal Carcinoma: Confirmation of Prognostic Significance and Histologic Cutoff in a Population-based Cohort," The American journal of surgical pathology, vol. 39, pp. 1340-1346, 2015.

V. H. Koelzer, I. Zlobec, M. D. Berger, G. Cathomas, H. Dawson, K. Dirschmid, et al., "Tumor budding in colorectal cancer revisited: results of a multicenter interobserver study," Virchows Archiv, vol. 466, pp. 485-493, 2015.

V. H. Koelzer, I. Zlobec, and A. Lugli, "Tumor budding in colorectal cancer—ready for diagnostic practice," Human pathology, vol. 47, pp. 4-19, 2016.

F. Petrelli, E. Pezzica, M. Cabiddu, A. Coinu, K. Borgonovo, M. Ghilardi, et al., "Tumour budding and survival in stage II colorectal cancer: A systematic review and pooled analysis," Journal of gastrointestinal cancer, vol. 46, pp. 212-218, 2015.

F. Grizzi, G. Celesti, G. Basso, and L. Laghi, "Tumor budding as a potential histopathological biomarker in colorectal cancer: Hype or hope?," World Journal of Gastroenterology: WJG, vol. 18, p. 6532, 2012.

R. L. Siegel, K. D. Miller, S. A. Fedewa, D. J. Ahnen, R. G. Meester, A. Barzi, et al., "Colorectal cancer statistics, 2017," CA: a cancer journal for clinicians, vol. 67, pp. 177-193, 2017.

V. H. Koelzer, N. Assarzadegan, H. Dawson, B. Mitrovic, A. Grin, D. E. Messenger, et al., "Cytokeratin-based assessment of tumour budding in colorectal cancer: Analysis in stage II patients and prospective diagnostic experience," The Journal of Pathology: Clinical Research. 2017, 171-178.

G. Rieger, V. H. Koelzer, H. E. Dawson, M. D. Berger, M. Hädrich, D. Inderbitzin, et al., "Comprehensive assessment of tumour budding by cytokeratin staining in colorectal cancer," Histopathology, vol. 70, pp. 1044-1051, 2017.

A. Gordon, G. Glazko, X. Qiu, and A. Yakovlev, "Control of the mean number of false discoveries, Bonferroni and stability of multiple testing," The Annals of Applied Statistics, pp. 179-190, 2007.

E. L. Korn and B. Freidlin, "A note on controlling the No. of false positives," Biometrics, vol. 64, pp. 227-231, 2008.

Siegel, R. L., et al. (2021). Colorectal cancer statistics, 2021. CA: A Cancer Journal for Clinicians, 71(3), 145-164.

V. H. Koelzer et al., "Tumor budding in colorectal cancer revisited: results of a multicenter interobserver study," Virchows Archiv, vol. 466, No. 5, pp. 485-493, 2015.

K. Kai et al., "Cytokeratin immunohistochemistry improves interobserver variability between unskilled pathologists in the evaluation of tumor budding in T1 colorectal cancer," Pathology international, vol. 66, No. 2, pp. 75-82, 2016.

G. Rieger et al., "Comprehensive assessment of tumour budding by cytokeratin staining in colorectal cancer," Histopathology, vol. 70, No. 7, pp. 1044-1051, 2017.

A. Lugli et al., "Recommendations for reporting tumor budding in colorectal cancer based on the International Tumor Budding Consensus Conference (ITBCC) 2016," Modern Pathology, vol. 30, No. 9, p. 1299, 2017.

Z. Liu et al., "Swin transformer: Hierarchical vision transformer using shifted windows," arXiv preprint arXiv:2103.14030, 2021.

A. Dosovitskiy et al., "An image is worth 16x16 words: Transformers for image recognition at scale," arXiv preprint arXiv:2010.11929, 2020.

A. Vaswani et al., "Attention is all you need," pp. 5998-6008.

D. Mattes, D. R. Haynor, H. Vesselle, T. K. Lewellyn, and W. Eubank, "Nonrigid multimodality image registration," in Medical Imaging 2001: Image Processing, 2001, vol. 4322, pp. 1609-1620: International Society for Optics and Photonics.

S. Rahunathan, D. Stredney, P. Schmalbrock, and B. D. Clymer, "Image registration using rigid registration and maximization of mutual information."

M. Styner, C. Brechbuhler, G. Szckely, and G. Gerig, "Parametric estimate of intensity inhomogeneities applied to MRI," IEEE transactions on medical imaging, vol. 19, No. 3, pp. 153-165, 2000.

M. K. Khan Niazi, M. M. Yearsley, X. Zhou, W. L. Frankel, and M. N. Gurcan, "Perceptual clustering for automatic hotspot detection from Ki-67-stained neuroendocrine tumour images," Journal of microscopy, vol. 256, No. 3, pp. 213-225, 2014.

(56) References Cited

OTHER PUBLICATIONS

S. Graham et al., "Hover-net: Simultaneous segmentation and classification of nuclei in multi-tissue histology images," Medical Image Analysis, vol. 58, p. 101563, 2019.

L.-C. Chen, G. Papandreou, F. Schroff, and H. Adam, "Rethinking atrous convolution for semantic image segmentation," arXiv preprint arXiv:1706.05587, 2017.

P. D. Caie, A. K. Turnbull, S. M. Farrington, A. Oniscu, and D. J. Harrison, "Quantification of tumour budding, lymphatic vessel density and invasion through image analysis in colorectal cancer," Journal of translational medicine, vol. 12, No. 1, p. 156, 2014.

N. J. Pedersen et al., "Construction of a pathological risk model of occult lymph node metastases for prognostication by semi-automated image analysis of tumor budding in early-stage oral squamous cell carcinoma," Oncotarget, vol. 8, No. 11, p. 18227, 2017.

C.-A. Weis et al., "Automatic evaluation of tumor budding in immunohistochemically stained colorectal carcinomas and correlation to clinical outcome," Diagnostic pathology, vol. 13, No. 1, p. 64, 2018.

R. K. Jepsen et al., "Digital image analysis of pan-cytokeratin stained tumor slides for evaluation of tumor budding in pT1/pT2 colorectal cancer: Results of a feasibility study," Pathology-Research and Practice, vol. 214, No. 9, pp. 1273-1281, 2018.

N. Brieu, C. G. Gavriel, I. P. Nearchou, D. J. Harrison, G. Schmidt, and P. D. Caie, "Automated tumour budding quantification by machine learning augments TNM staging in muscle-invasive bladder cancer prognosis," Scientific reports, vol. 9, No. 1, p. 5174, 2019.

I. P. Nearchou, K. Lillard, C. G. Gavriel, H. Ueno, D. J. Harrison, and P. D. Caie, "Automated Analysis of Lymphocytic Infiltration, Tumor Budding, and Their Spatial Relationship Improves Prognostic Accuracy in Colorectal Cancer," Cancer immunology research, vol. 7, No. 4, pp. 609-620, 2019.

* cited by examiner

CREATING A TUMOR BUD GROUND TRUTH OF H AND E STAINED SLIDES AND AUTOMATED IDENTIFICATION OF TUMOR BUDS USING AN H AND E STAINED SLIDES

CROSS-REFERENCE TO RELATED APPLICATION

This application is a national stage application filed under 35 U.S.C. § 371 of PCT/US2023/060973 filed Jan. 20, 2023, which claims priority to and benefit of U.S. provisional patent application 63/301,353 filed Jan. 20, 2022, which is fully incorporated by reference and made a part hereof.

FIELD OF THE INVENTION

The present disclosure relates to the detection of tumor buds in tumors and more specifically, to an automated analysis of histology images of sectioned and stained tumors to detect areas of tumor budding.

BACKGROUND

Tumor budding (TB) has emerged as an important adverse prognostic factor for increasing number of different cancer types, including colorectal cancer, head and neck squamous cell carcinoma [1, 2], breast cancer [3], esophageal cancer [4], gastric cancer [5, 6], and cervical cancer [7, 8]. In multiple recent studies of colorectal cancer, tumor budding [9-16] has been associated with higher tumor stage, lymph node metastasis, and decreased disease-free survival. Additionally, tumor budding has been included as a reportable feature in the Colorectal Cancer (CRC) Protocol published by the College of American Pathologists.

Tumor budding is defined as the presence of single tumor cells or small tumor clusters (e.g., up to 4 cells) that "bud" from the invasive front of the main tumor [17]. Tumor budding is believed to represent a type of epithelial-to-mesenchymal transition, in that the tumor cells gained migratory capability by loss of cell-to-cell adhesions and polarity. Thus, tumor budding is the first biologic step towards metastasis. In colorectal carcinoma, for example, tumor budding has been associated with tumors having an aggressive biology. Additionally, tumor budding, in cases of colorectal cancer, has been independently associated with poor treatment outcome, lymph node metastasis, and high recurrence [18]. Because tumor budding has been associated with poor treatment outcomes, identification of tumor budding in colorectal cancers (e.g., via endoscopically-resected malignant polyps) is important at an early stage so that more aggressive management may be considered.

According to the American Cancer Society, colorectal cancer (CRC) is the third most common cancer and the second leading cause of cancer death in the United States, with an estimated incidence of 149,500 new cases in 12021 [24]. Identification of tumor budding (TB) in CRCs is important, as TB has been associated with poor outcomes and can be used as a biomarker for better patient risk stratification. In CRC, TB it is recognized as a valuable prognostic factor, but its routine clinical use is hampered by a lack of agreement on the optimal method of assessment. The College of American Pathologists (CAP) Cancer Protocol and International Tumor Budding Consensus Conference (ITBCC) guidelines suggest that it be performed on the hematoxylin & eosin (H&E) slide. However, numerous studies have shown that identifying tumor buds on an H&E slide is difficult and is nearly irreproducible [25, 26]. Identifying tumor budding by manual methods requires close evaluation of the tumor invasive front using intermediate to high power magnification, which is subjective. Assessment of tumor budding (i.e., tumor bud identification) by manual methods requires close evaluation of the tumor invasive front under intermediate to high power (e.g., 200 or 400 times) magnification. This manual assessment; however, is time-consuming and subjective, which could hinder it from becoming a routine procedure in diagnosing and treating common cancers. This diagnostic subjectivity creates a critical barrier to progress in effectively using this important prognostic factor in cancer evaluation.

While H&E staining is the gold standard in histological diagnosis of CRC, recent findings have suggested the use of pan-cytokeratin (AE1/3) immunostaining for the evaluation of TB can increase TB counts three to six times when compared to H&E staining. For example, in a multi-institutional study, Koelzer found that the inter-observer agreement among pathologists was excellent (>80%) for identifying TB using AE1/3 in CRC patients. In contrast, the agreement dropped to 58% when TB was assessed on H&E slides [25]. They concluded that assessment of TB on AE1/3 slides is feasible in a large pathology institute and leads to expected associations with clinic-pathological features. Furthermore, Rieger et al. found that inter-observer reproducibility was markedly improved with AE1/3 staining. This is due in part to the fact that AE1/3 specifically highlights epithelial cells while helping to distinguish epithelial cells from reactive stromal cells and inflammation.

However, while AE1/3 immunostaining facilitates TB evaluation, it is not routinely used in evaluating CRC. CAP and ITBCC recommend that tumor bud counts should be done on H&E sections. However, CAP recommends that immunohistochemistry should be obtained in difficult cases with obscuring inflammation to facilitate TB evaluation, but the scoring should be done on H&E sections. Unfortunately, the cost and time of AE1/3 make it less efficient in routine clinical settings. For these reasons, an image analysis method that learns from AE1/3 and H&E during training but only relies on H&E during testing and deployment is desired.

A need, therefore, exists for automating the process of tumor bud identification, not just for evaluation of colorectal cancer, but also for an increasing number of other cancer types.

SUMMARY

Accordingly, the present disclosure encompasses an automated image analysis method for detecting and quantifying tumor budding in H&E stained tumors that benefits from training an artificial intelligence (AI) algorithm using a dataset of H&E slides. The results of the tumor budding identification may be used to guide or facilitate human analysis and/or may be used to predict a clinical outcome.

Disclosed and described herein is a method of detecting tumor budding. First, adjacent AE1/3 and H&E are registered in order to provide a reliable ground truth for tumor regions and TB. The identification of tumor invasive front from tumor regions is carried out by alpha shapes. Second, swin transformers are utilized to segment malignant tumor regions on H&E images. As TB should be assessed at the tumor invasive front, identifying the tumor invasive front helps to narrow the search region for TB. Third, a series of automatic post-processing steps transfer small positive regions identified on AE1/3 (potential tumor buds) onto registered H&E, where they are filtered by number of nuclei. This yields TB on H&E that benefit from registered AE1/3.

The method may be implemented using a support vector machine or a neural network as the machine learning classifier. Additionally, the textual and spatial features may include local binary patterns, histograms of oriented gradients, or multiresolution Shearlet transforms. Further, in a possible implementation, the training process may include deep learning.

In another instance, a weakly-supervised machine learning method is used where tumor budding labels are assigned to collections (called bags) rather than individual examples (called instances), where bags are comprised of tessellated whole-slide images (WSIs), in which each instance is a small unannotated image sampled from the WSI. In this manner, only slide-level labels are required for its training and implementation, thus negating the need for tissue-level annotations.

The foregoing illustrative summary, as well as other exemplary objectives and/or advantages of the disclosure, and the manner in which the same are accomplished, are further explained within the following detailed description and its accompanying drawings.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

FIGS. 3A-C are images corresponding to intermediate steps in the method of FIG. 1, wherein FIG. 3A is a binary image depicting tissue areas corresponding to the image of FIG. 1, FIG. 3B depicts detected nuclei within the tissue areas, and FIG. 3C is a binary image depicting identified tumor buds corresponding to the image of FIG. 1.

DETAILED DESCRIPTION

Recent findings have suggested the use of pan-cytokeratin (AE1/3) immunostaining for the evaluation of tumor budding is feasible in daily diagnostic practice [20]. A study by the Swiss Association of Gastrointestinal Pathology in 2016 found that tumor budding counts are three to six times greater upon pan-cytokeratin staining compared to the standard H&E staining. The same study also found that interobserver reproducibility was markedly improved with pan-cytokeratin staining compared to H&E. Koelzer and Rieger et al. [21] [8] presented a comprehensive assessment of tumor budding by cytokeratin staining in colorectal cancer. Koelzer [20] also concluded that assessment of tumor budding on pan-cytokeratin slides is feasible in a large pathology institute and leads to expected associations with clinic-pathological features. AE1/3 specifically highlights tumor cells while de-emphasizing background non-epithelial cells, making it very useful in computer assisted tumor budding assessment.

Tumor Bud Identification in Pan-Cytokeratin AE1/3 Images

Figure 1:
FIG. 1 is an example image of a pan-cytokeratin AE1/3 stained section of a tumor under magnification.
Figure 2:
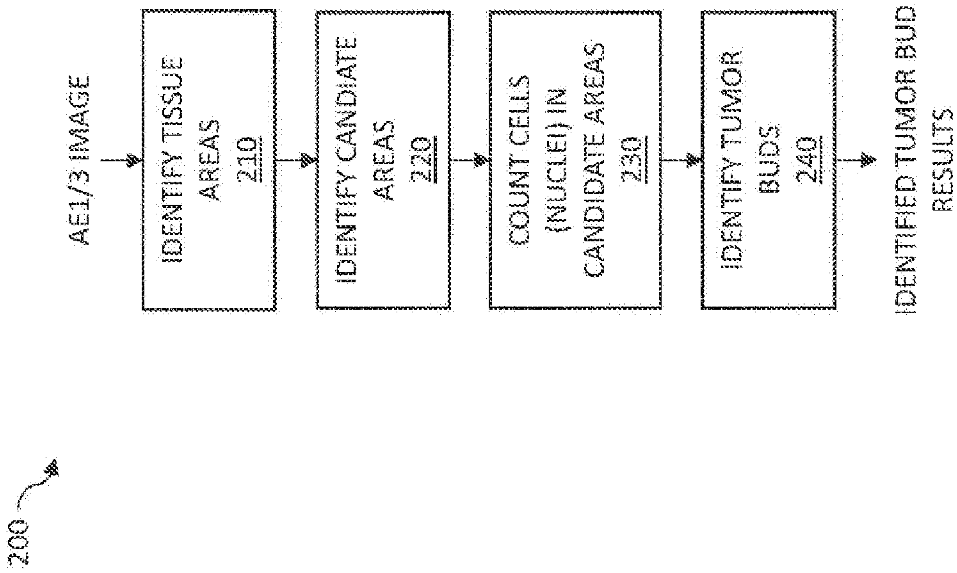
FIG. 2 is a flow chart depicting an exemplary method for identifying tumor buds in an image of a pan-cytokeratin AE1/3 stained section of a tumor.

An image of a pan-cytokeratin AE1/3 stained section of a tumor is shown in FIG. 1. As shown, the cytoplasm of cells is stained brown (dark), nuclei are counterstained blue (light), and a background region is white. A method 200 for identifying tumor buds in the image (FIG. 1) generally comprises the operations of tissue segmentation to identify tissue areas 210, filtering the identified tissue areas by size to identify candidate areas 220, counting nuclei (i.e., cells) in the candidate areas 230, and identifying tumor buds based on the number of cells in the candidate areas 240.

Tissue segmentation to identify tissue areas may use thresholding to distinguish nuclei tissue from the background and from debris (e.g., necrotic tissues). Additionally, noise and small spurious segments from debris may be removed in the segmentation process. This removal is especially important when debris or necrotic tissues are present in the image. This noise removal may use an adjustable threshold, but care should be taken that it is not selected too large because potential tumor buds may be removed.

Segmentation may use an automatic thresholding in which the threshold is computed using Otsu's method. In a typical embodiment, initial parameters are provided to an Otsu thresholding algorithm. The initial parameters provided to the Otsu thresholding algorithm may include an Otsu threshold of t=64 pixels and an Otsu weight w=1.25. These parameters may be selected optimally as a study requires.

Additionally, identifying tissue areas 200 may require morphological operations (e.g., dilation, filling, and erosion) to correct for thresholding errors and provide the identification of tissue areas.

Figure 3A:
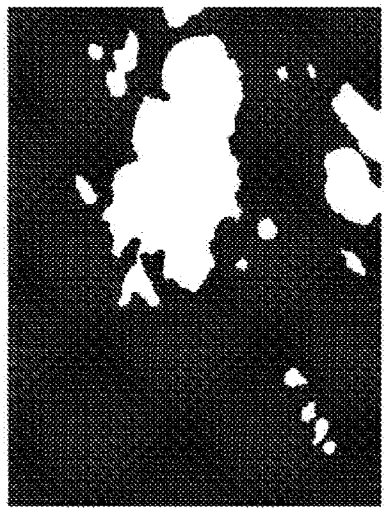

FIG. 3A illustrates the results of tissue segmentation (i.e., identification of tissue areas) for the image of FIG. 1. As shown, the results include a binary image, wherein pixels corresponding to tissues area white and pixels not corresponding to tissue (e.g., debris, background, etc.) are black. This binary image may be used to determine the areas in the image (FIG. 1) that correspond to tissues.

The tissue areas may be filtered in terms of size to identify candidate areas likely to contain tumor buds (i.e., candidate areas). The size of each candidate area should not be too small or too large. Accordingly, two threshold values $n_1$ and $n_2$ are used to identify candidate areas from the tissue areas. Regions smaller than $n_1$ are likely to be noise (e.g., due to imperfect staining), while regions larger than $n_2$ are likely to be another tissue component (e.g., fat). In a typical implementation, thresholds of $n_1$=16 and $n_2$=4096 pixels may be used to identify the candidate areas from the tissue areas. In the example shown in FIG. 3A, the tissue areas are all identified as candidate areas. These threshold values may be optimized based on the application.

Figure 3B:
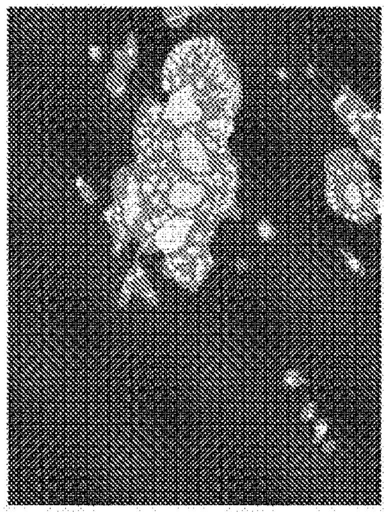

To identify tumor buds, cells within each candidate area may be counted and compared to a range. Because nuclei indicate a cell, nuclei detection forms the basis of cell counting. FIG. 3B shows the candidate areas of FIG. 3A with detected nuclei (shown as light gray).

As mentioned previously, AE1/3 staining highlights the tumor budding cells while de-emphasizing non-epithelial cells, hence the detected nuclei from the operations of segmentation and nuclei detection are all tumor cells. After nuclei detection, cell counting (i.e., nuclei counting) within the candidate areas is performed and candidate areas with a cell count in a range of one to four cells may be identified as tumor buds. Additionally, tissue segments with more than four cells may be identified as part of the main tumor. The number of nuclei used to identify a tumor bud may be optimized based on the application.

Tissue cells with no visible nuclei are not immediately classified tumor buds but are considered exceptions that require further analysis. Accordingly, tissue segments with no detected cells (i.e., nuclei), can be further analyzed in terms of the shape and intensity of the tissue. For example, tissue regions having no visible nuclei that also have a high average intensity and a high degree of circularity may be identified as tumor buds.

Figure 3C:
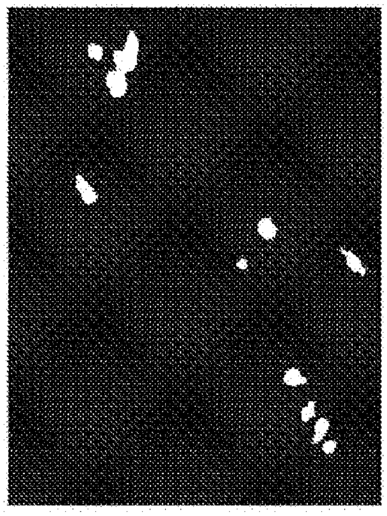

FIG. 3C illustrates the tumor buds identified from an analysis of FIG. 3B. The tumor buds are candidate areas that meet the cell count and size/shape criteria described above. Using this binary image of tumor buds, results may be generated and presented.

Figure 4:
FIG. 4 illustrates exemplary results of tumor bud identification, wherein the image of FIG. 1 is shown with indications of identified tumor buds.

FIG. 4 illustrates the image of FIG. 1 with indications of tumor buds. Additional results may also be generated. The results may include a count of the number of tumor buds and the relative location of tumor buds. The results may be presented to a user and may guide the user in a visual analysis of the tumor section. Further, in some cases, the results may replace a manual analysis of the image (or slide) by a human.

While AE1/3 staining facilitates tumor budding evaluation, it is not used routinely in evaluating colorectal cancer. College of American Pathologists Cancer Protocol and International Tumor Budding Consensus Conference (ITBCC, 2016) recommend the following [17]:

> "Tumor budding counts should be done on H&E sections. In cases of obscuring factors like inflammation, immunohistochemistry for keratin can be obtained to assess the advancing edge for tumor buds, but the scoring should be done on H&E sections."

Accordingly, the present disclosure also embraces a method for detecting tumor buds in images of hematoxylin and eosin (H&E) stained slides.

Tumor Bud Identification in Hematoxylin and Eosin (H&E) Images

Described in this section is a method for identifying tumor buds in an image of a hematoxylin & eosin (H&E) stained section of a tumor. Generally, the method comprises creating a ground truth of H&E stained slides having identified regions of tumor buds and/or identified regions that are not tumor buds; training an artificial intelligence (AI) algorithm using the dataset of H&E stained slides; and analyzing the image of the H&E stained section of the tumor using the trained AI algorithm to determine a presence or absence of tumor buds on the H&E stained slide from the patient.

Generally, the following section focuses on creating the ground truth of H&E stained slides having identified regions of tumor buds and/or identified regions that are not tumor buds. Broadly, this comprises registering adjacent AE1/3 and H&E in order to provide a reliable ground truth for tumor regions and tumor budding; swin transformers are utilized to segment malignant tumor regions on one or more H&E images; and the segmented malignant tumor regions found by the swin transformers on the one or more H&E images are verified, wherein a series of automatic post-processing steps transfer small positive regions identified on AE1/3 (potential tumor buds) onto registered H&E, where they are filtered by number of nuclei to determine if they comprise a tumor bud. In some instances, the above-mentioned AI algorithm comprises a swin transformer.

Materials and Methods

Datasets

Figure 5:
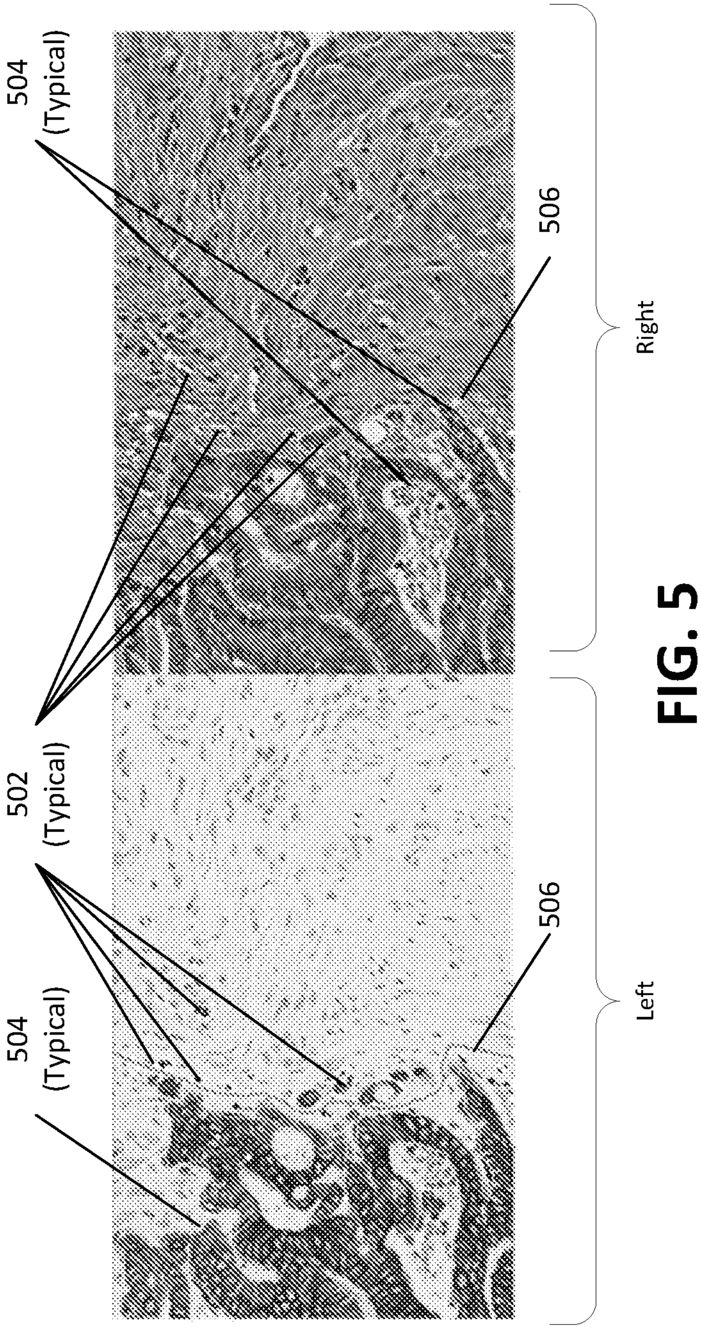
FIG. 5 illustrates manually-registered, adjacent AE1/3 (left) and H&E (right) HPFs, which have been annotated for tumor buds (yellow, 502), malignant glands (green, 504), and tumor invasive front (red, 506).

One exemplary, non-limiting dataset comprises of 120 adjacent AE1/3 and H&E tissue slides. All slides were anonymized and digitized at 40× magnification using a high-resolution scanner (Aperio ScanScope XT, Vista, California) at 0.061 microns per pixel squared. Pathologists manually registered a subset of 10 pairs of tissue slides in order to extract 109 adjacent high-power fields (HPFs) which contain tumor buds. Approximately 11 HPFs were extracted per slide. FIG. 5, below, depicts an example of annotated, manually-registered, adjacent HPFs. Similarly, pathologists manually registered all pairs of tissue images in order to extract 648 adjacent HPFs. This latter set was annotated for tumor-positive and tumor-negative regions on H&E.

Swin Transformers

Swin transformers operate based on a recent state-of-the-art classification models known as vision transformers [30]. These transformer models differentiate themselves from traditional convolutional neural networks (CNNs) by forgoing convolutions in favor of natural language processing based "attention" [31]. The swin transformer takes a step further by learning multiple scales of an input image through a shifted-window approach on concatenated embeddings and includes a module decoding network for semantic segmentation.

Using the official implementation, each transformer was trained for 40,000 iterations using transfer learning from ImageNet weights. Segmentation results were evaluated using pixel-wise accuracy and intersection over union (IoU) for tumor and non-tumor classes. This was carried out using a five-fold cross-validation across 120 slides on the set of 648 HPFs.

Positive Region Identification on H&E

Figure 6:
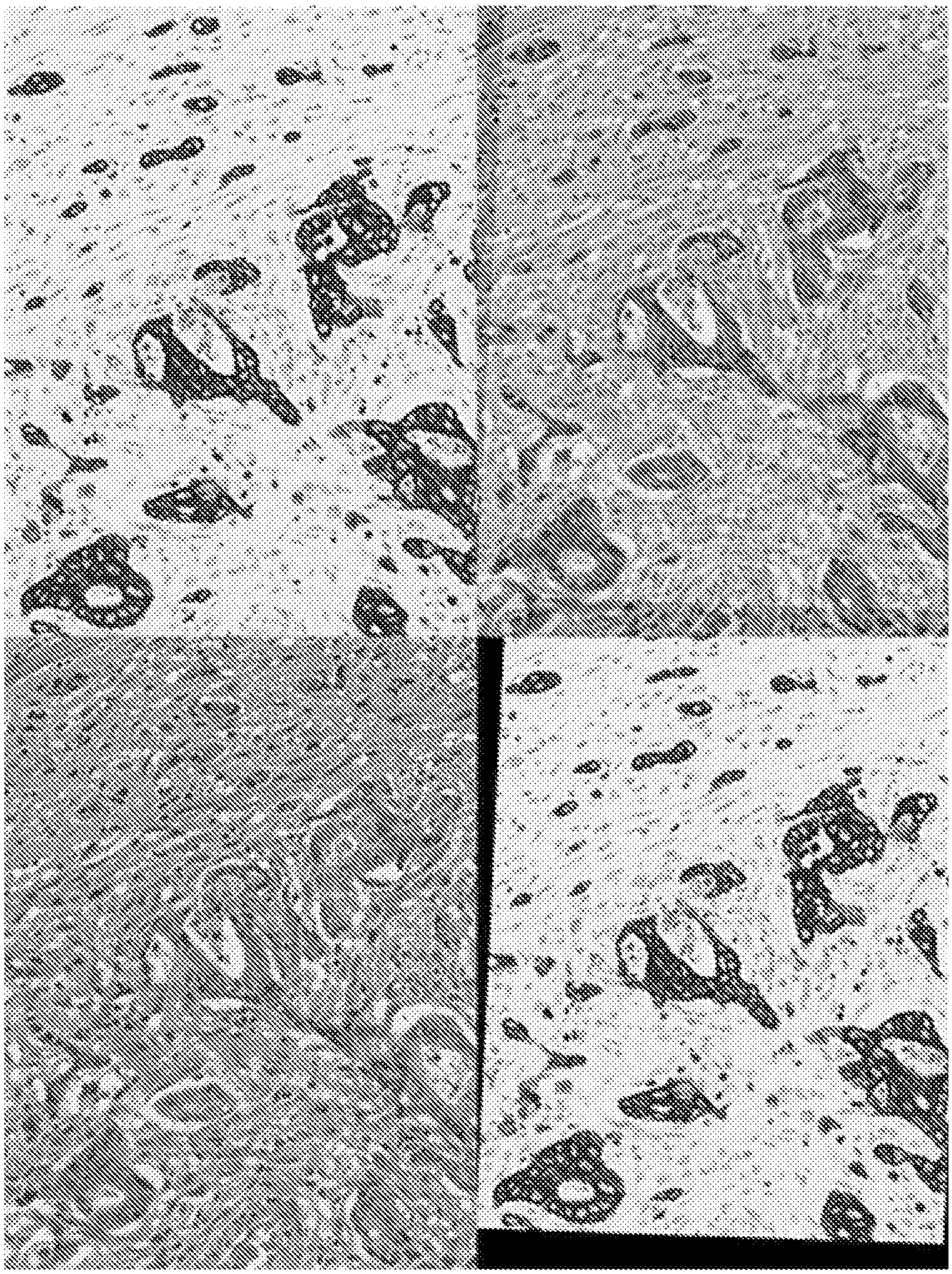
FIG. 6 illustrates an example of automatically registered adjacent HPFs—H&E (top left), AE1/3 (top right), registered AE1/3 (bottom left), composite image (bottom right).

Given that manual registration methods by pathologists are completely rigid and may not result in complete overlap between adjacent sections due to deformations, automatic non-rigid image registration techniques were utilized to deform the AE1/3 images to maximize overlap with adjacent H&E image. Mattes mutual information was used as a metric [32, 33], and a one-plus-one evolutionary algorithm was used as an optimizer. An example of the resulting registered images is depicted in FIG. 6.

Figure 7:
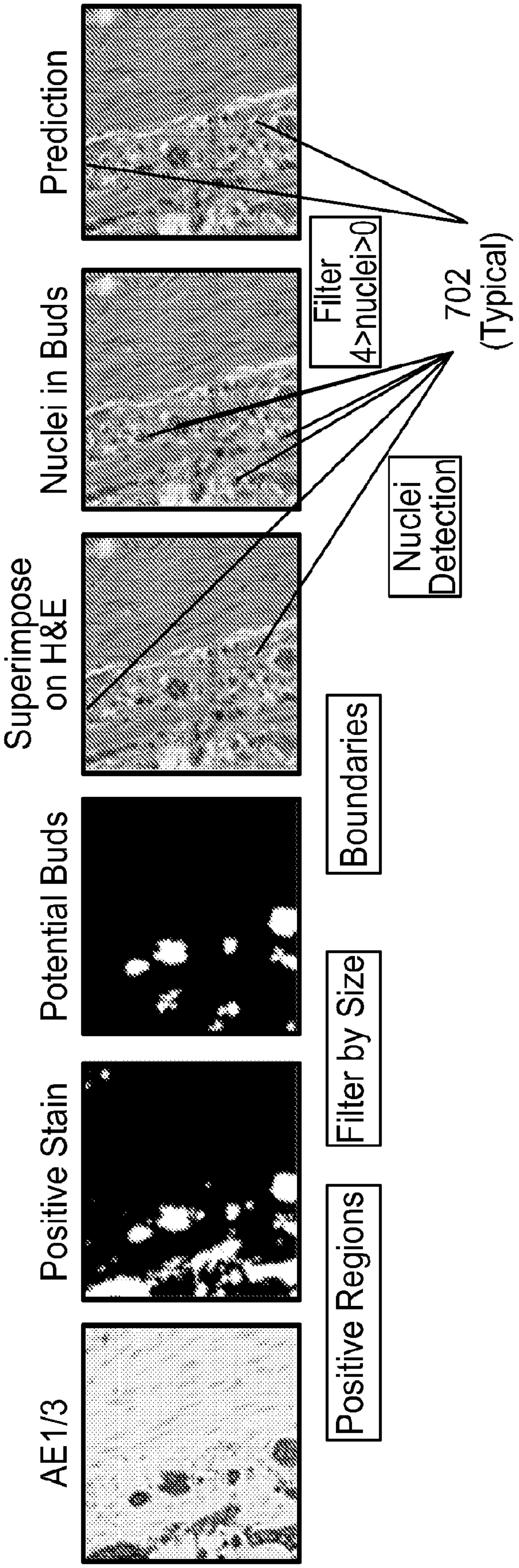
FIG. 7 illustrates post-processing steps including image registration to transfer positive regions of AE1/3 on to H&E to yield tumor buds. Registration of positive region mask is omitted. Tumor nuclei shown in red 702 (nuclei detection).

Positive stained regions of AE1/3 HPFs were identified using a method developed by Niazi et al. [35]. To filter out any spurious staining and glands, an area filter was passed over the resulting positive region mask. Only objects between 1000 and 10000 pixels were retained. Next, the same non-rigid transformation learned from the previous registration step was applied to the positive region mask. The resulting locations of positive regions were transferred to adjacent H&E as potential tumor bud locations. Subsequently, automatic nuclei detection was performed within positive regions on adjacent H&E sections using hover-net [36]. As TB only contain between one to four nuclei, transferred positive regions with zero or more than four nuclei were discarded. These steps are summarized in FIG. 7.

To check concordance of tumor buds between AE1/3 and H&E, pathologist-generated AE1/3 tumor budding annotation masks were registered to H&E using same transformation function computed from adjacent sections.

RESULTS

Table 1 reports the results of five-fold cross-validation for tumor region detection across 648 H&E HPFs from 120 slides.

TABLE 1

Performance metrics for tumor region detection.

| | | fold 1 | fold 2 | fold 3 | fold 4 | fold 5 | mean ± std |
|---|---|---|---|---|---|---|---|
| Accuracy | tumor | 0.9458 | 0.9689 | 0.9328 | 0.9694 | 0.9696 | 0.9573 ± 0.0171 |
| | non-tumor | 0.9937 | 0.9853 | 0.9919 | 0.9896 | 0.9908 | 0.9903 ± 0.0032 |
| IoU | tumor | 0.9250 | 0.9251 | 0.9094 | 0.9689 | 0.9399 | 0.9337 ± 0.0226 |
| | non-tumor | 0.9789 | 0.9759 | 0.9714 | 0.9800 | 0.9820 | 0.9776 ± 0.0041 |

Overall, tumor and non-tumor segmentation accuracy and IoU is high. These accuracies exceed to those of more conventional methods, such as DeepLabv3 [37] (not reported).

To assess the performance of our tumor budding ground-truth generation algorithm, precision and recall metrics were computed on bounding boxes of detected regions. A tumor bud was considered successfully detected if there was at least 50% overlap between a bounding box of the method and the ground truth generated by pathologists. Table 2 reports these results.

TABLE 2

Tumor budding precision and recall.

| | Proposed vs. H&E | Proposed vs. AE1/3 | H&E vs AE1/3 |
|---|---|---|---|
| Precision | 0.3856 ± 0.2678 | 0.5966 ± 0.2826 | 0.3470 ± 0.2628 |
| Recall | 0.3254 ± 0.2312 | 0.2735 ± 0.1582 | 0.1932 ± 0.1700 |

In Table 2, "Proposed" refers to the proposed method. "H&E" and "AE1/3" refers to the ground truth generated by pathologists using respective adjacent HPFs.

Although metrics values for the proposed method seem low, it is worth pointing out that on average, precision and recall between the proposed method and either ground truth generated by pathologists are greater than the precision and recall when considering AE1/3 as a ground truth vs. H&E and as prediction. This may be explained by the biases afforded by both stains. Discriminating inflammatory cells (histocytes) and stromal cells (activated fibroblasts/myofibroblasts) from TB may be difficult on AE1/3, leading to a bias towards false positives. Conversely, factors such as inflammation may obscure TB on H&E, leading to false negatives. Theoretically, if the proposed method had fewer false positives than AE1/3 and fewer false negatives than H&E, then results as in Table 2 would be observed. In other words, the proposed method serves as a kind of middle ground between pathologist evaluation on H&E and pathologist evaluation on AE1/3, agreeing with pathologist evaluation on H&E and pathologist evaluation on AE1/3 individually more than pathologist evaluation on AE1/3 agrees with pathologist evaluation on H&E.

Image analysis of tumor budding has been reported [15-20]. Yet, none of these analyses was performed using H&E slides alone. All of these studies employed specially stained slides like AE1/3 (immunohistochemistry or immunofluorescence) that are not routinely used in clinical evaluation tumor budding. By generating a reliable ground truth for TB on H&E that benefits from AE1/3, algorithms that can detect TB on routine H&E slides alone can be created and/or trained, which will be easily incorporated into clinical practice without the extra step of special stains.

Here, swin transforms are presented as a method to detect tumor regions in CRC H&E images. In an example, the method was highly accurate during cross-validation, achieving on average 95% accuracy for tumor regions and 99% accuracy for non-tumor regions. Also presented is a preliminary method to generate tumor budding ground truth from H&E images. The average precision and recall compared to pathologist annotations was 0.3856 and 0.3254, which exceeded precision and recall of 0.3470 and 0.1932 from pathologist-annotated AE1/3. These results provide preliminary evidence for the feasibility of the disclosed method to generate ground truth for tumor budding on H&E stained slides while benefiting from AE1/3.

Minimizing the Intra-Pathologist Disagreement for Tumor Bud Detection on H&E Images Using Weakly Supervised Learning Multiple-instance learning (MIL) is a weakly-supervised machine learning method where labels are assigned to collections (called bags) rather than individual examples (called instances), as in conventional machine learning. For histopathological analyses, bags are comprised of tessellated whole-slide images (WSIs), in which each tile is a small unannotated image sampled from the WSI. It is popular for WSI analyses, as only slide-level labels are required for its training and implementation, thus negating the need for tissue-level annotations.

Arguably the most successful adaptation of MIL within WSI analysis is attention-based (AB) MIL. The attention-based pooling mechanism automatically learns to weight embedded instances into a bag-level feature vector dynamically. A weight is automatically computed for each embedded instance, then a weighted sum combines them into a single, bag-level instance, corresponding to a slide-level embedding. Classification or regression is then performed on this bag-level embedding.

$$a_k = \frac{\exp\{w^T \tanh(Vh_k^T) \cdot sigm(Uh_k^T)\}}{\sum_{j=1}^{K} \exp\{w^T \tanh(Vh_j^T) \cdot sigm(Uh_k^T)\}} \quad (1)$$

$$z = \sum_{k=1}^{K} a_k h_k \quad (2)$$

The attention mechanism implementation comprises a simple two-layer fully connected network that passes each instance embedding ($h_k$) through two parallel layers of the network (V,U), applies a tanh and sigmoid activation function to the respective results, dots the results, then passes the fused activation through another layer ($w^T$), which maps the vector into a single value, its attention weight ($a_k$). Equation 1, above, summarizes these interactions. The weighted sum of each embedded instance and its attention weight yields a bag-level instance (z), as depicted in Equation 2. The parameters (V, U, w) for this two-layer neural network are automatically learned through model training. For example, SqueezeNet (F. N. Iandola, S. Han, M. W. Moskewicz, K. Ashraf, W. J. Dally, and K. Keutzer, "SqueezeNet: AlexNet-level accuracy with 50× fewer parameters and <0.5 MB model size," arXiv preprint arXiv: 1602.07360, 2016—incorporated by reference) pretrained on ImageNet as a feature extractor to generate instance embeddings ($h_k$) may be utilized. This network was attached to the attention mechanism and trained end-to-end.

Initially, a tumor was segmented using a previously published method (T. E. Tavolara et al., "Automatic generation of the ground truth for tumor budding using H&E stained slides," in SPIE Medical Imaging 2022: Digital Pathology, 2022 2022, vol. 12039: SPIE, pp. 40-46—incorporated by reference), and removed from WSIs. As mentioned earlier, TBs were annotated by pathologists. TB bags were created by first cropping a 512×512 pixel region surrounding each tumor bud, then second cropping 96×96 pixel instances with a stride of 32 pixels from within this region. Tessellating 512×512 pixel regions created non-tumor bags within annotated non-tumor regions into 96×96 pixel instances. In this manner, each 512×512 pixel region served as a "bag," and the 96×96 pixel crops from each region served as instances of respective bags. An ROI size of 96×96 pixels was chosen according to the maximum expected size of a tumor bud. In total, there were 3344 TB bags and 5573 non-tumor bags. This process is depicted in FIG. 8.

Figure 8:
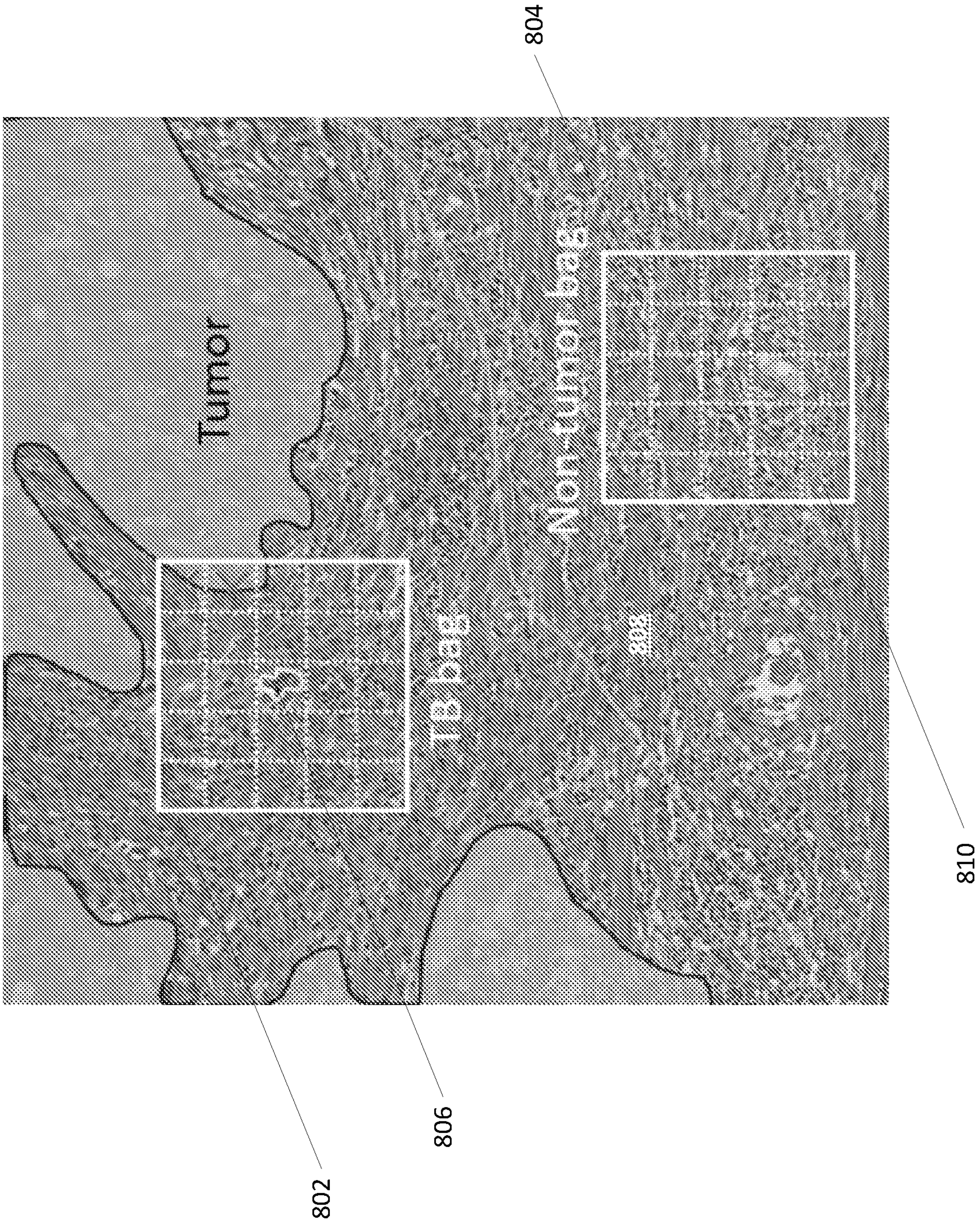
FIG. 8 illustrates tumor budding (TB) and non-tumor bag creation where the shown exemplary bags are 512×512 pixel regions around annotated tumor buds or within annotated non-tumor regions which are tessellated into 96×96 pixel instances, and instances with tumor are excluded (cross).

FIG. 8 illustrates tumor budding (TB) and non-tumor bag creation where the shown exemplary bags are 512×512 pixel regions 802, 804 around annotated tumor buds 806 or within annotated non-tumor regions 808 which are tessellated into 96×96 pixel instances 810, and instances with tumor are excluded (shown by crosses).

Six-fold cross-validation was performed in which each set served as a training, validation, or testing set. In each fold, slides were randomly split into three sets (10/10/9). Models were optimized using Adam with β1=0.9 and β2=0.999, the learning rate of 0.0001, weight decay of 0.0005, and over 100 epochs. Models resulting in the lowest validation loss were applied to respective testing sets. The resulting precision, recall, and AUC were recorded. A Faster R-CNN Field was applied as a comparison method with a pre-trained ResNet50 backbone.

Table 3, below, reports the results of attention-based MIL (AB-MIL) and Faster R-CNN The proposed AB-MIL method resulted in a precision of 0.7705±0.0978, recall of 0.9089±0.0535, and AUC of 0.9311±0.0481. Faster R-CNN resulted in a precision of and a recall of 0.3837±0.0374 and 0.4447±0.0478, respectively. AUC measurements were unavailable for Faster R-CNN, as a negative ROI or background class did not exist. As a comparison, pathologist precision and recall after the washout period is around 0.6754±0.3253 and 0.3060±0.2014 based on previous studies.

TABLE 3

Results of attention-based MIL (AB-MIL) and Faster R-CNN.

| | | Precision | Recall | AUC |
|---|---|---|---|---|
| Validation | AB-MIL | 0.7705 ± 0.0978 | 0.9119 ± 0.0587 | 0.9271 ± 0.0562 |
| | Faster R-CNN | 0.3832 ± 0.0369 | 0.4461 ± 0.0386 | — |
| Testing | AB-MIL | 0.7698 ± 0.1104 | 0.9089 ± 0.0535 | 0.9311 ± 0.0481 |
| | Faster R-CNN | 0.3837 ± 0.0374 | 0.4447 ± 0.0478 | — |

Prior image analysis of TB employed specially stained slides like AE1/3 (immunohistochemistry or immunofluorescence) putting such methods at a disadvantage, as AE1/3 is not routinely used in the clinical evaluation of TB. However, a method is presented to detect TB using a weakly-supervised method that does not require strictly accurate tissue-level annotations. Attention-based multiple instance learning was applied to identify ROIs containing TB. This resulted in a precision of 0.7705±0.0978, recall of 0.9089±0.0535, and AUC of 0.9311±0.0481. These results provide preliminary evidence for the feasibility of the disclosed method to accurately identify TB and may overcome the limitations posed by previous methods reliance on AE1/3 for generating TB ground truth.

In the specification and/or figures, typical embodiments have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

Unless otherwise indicated, each of the below references are fully incorporated by reference and made a part hereof:

REFERENCES

[1] M. Boxberg, M. Jesinghaus, C. Dorfner, C. Mogler, E. Drecoll, A. Warth, et al., "Tumour budding activity and cell nest size determine patient outcome in oral squamous cell carcinoma: proposal for an adjusted grading system," Histopathology, vol. 70, pp. 1125-1137, 2017.

[2] P. V. Angadi, P. V. Patil, K. Hallikeri, M. Mallapur, S. Hallikerimath, and A. D. Kale, "Tumor budding is an independent prognostic factor for prediction of lymph node metastasis in oral squamous cell carcinoma," International journal of surgical pathology, vol. 23, pp. 102-110, 2015.

[3] X. Li, B. Wei, C. Sonmez, Z. Li, and L. Peng, "High tumor budding count is associated with adverse clinicopathologic features and poor prognosis in breast carcinoma," Human Pathology, 2017.

[4] M. Jesinghaus, M. Boxberg, B. Konukiewitz, J. Slotta-Huspenina, A. M. Schlitter, K. Steiger, et al., "A Novel Grading System Based on Tumor Budding and Cell Nest Size Is a Strong Predictor of Patient Outcome in Esophageal Squamous Cell Carcinoma," The American Journal of Surgical Pathology, vol. 41, pp. 1112-1120, 2017.

[5] K. Che, Y. Zhao, X. Qu, Z. Pang, Y. Ni, T. Zhang, et al., "Prognostic significance of tumor budding and single cell invasion in gastric adenocarcinoma," OncoTargets and therapy, vol. 10, p. 1039, 2017.

[6] S. Olsen, J. Linda, R. C. Fields, Y. Yan, and I. Nalbantoglu, "Tumor Budding in Intestinal Type Gastric Adenocarcinoma is Associated with Nodal Metastasis and Recurrence," Human Pathology, 2017.

[7] B. Huang, J. Cai, X. Xu, S. Guo, and Z. Wang, "High-Grade Tumor Budding Stratifies Early-Stage Cervical Cancer with Recurrence Risk," PloS one, vol. 11, p. e0166311, 2016.

[8] N. Satabongkoch, S. Khunamornpong, T. Pongsuvareeyakul, J. Settakorn, K. Sukpan, A. Soongkhaw, et al., "Prognostic Value of Tumor Budding in Early-Stage Cervical Adenocarcinomas," Asian Pacific journal of cancer prevention: AP JCP, vol. 18, p. 1717, 2017.

[9] Y. H. Lai, L. C. Wu, P. S. Li, W. H. Wu, S. B. Yang, P. Xia, et al., "Tumour budding is a reproducible index for risk stratification of patients with stage II colon cancer," Colorectal Disease, vol. 16, pp. 259-264, 2014.

[10] A. Mezheyeuski, I. Hrynchyk, M. Karlberg, A. Portyanko, L. Egevad, P. Ragnhammar, et al., "Image analysis-derived metrics of histomorphological complexity predicts prognosis and treatment response in stage II-III colon cancer," Scientific reports, vol. 6, p. 36149, 2016.

[11] I. Zlobec, M. Hädrich, H. Dawson, V. Koelzer, M. Borner, M. Mallaev, et al., "Intratumoural budding (ITB) in preoperative biopsies predicts the presence of lymph node and distant metastases in colon and rectal cancer patients," British journal of cancer, vol. 110, p. 1008, 2014.

[12] R. Cappellesso, C. Luchini, N. Veronese, M. L. Mele, E. Rosa-Rizzotto, E. Guido, et al., "Tumor Budding as a Risk Factor for Nodal Metastasis in Pt1 Colorectal Cancers: A Meta-Analysis," Human Pathology, 2017.

[13] R. P. Graham, R. A. Vierkant, L. S. Tillmans, A. H. Wang, P. W. Laird, D. J. Weisenberger, et al., "Tumor Budding in Colorectal Carcinoma: Confirmation of Prognostic Significance and Histologic Cutoff in a Population-based Cohort," The American journal of surgical pathology, vol. 39, pp. 1340-1346, 2015.

[14] V. H. Koelzer, I. Zlobec, M. D. Berger, G. Cathomas, H. Dawson, K. Dirschmid, et al., "Tumor budding in colorectal cancer revisited: results of a multicenter interobserver study," Virchows Archiv, vol. 466, pp. 485-493, 2015.

[15] V. H. Koelzer, I. Zlobec, and A. Lugli, "Tumor budding in colorectal cancer-ready for diagnostic practice," Human pathology, vol. 47, pp. 4-19, 2016.

[16] F. Petrelli, E. Pezzica, M. Cabiddu, A. Coinu, K. Borgonovo, M. Ghilardi, et al., "Tumour budding and survival in stage II colorectal cancer: A systematic review and pooled analysis," Journal of gastrointestinal cancer, vol. 46, pp. 212-218, 2015.

[17] A. Lugli, R. Kirsch, Y. Ajioka, F. Bosman, G. Cathomas, H. Dawson, et al., "Recommendations for reporting tumor budding in colorectal cancer based on the International Tumor Budding Consensus Conference (ITBCC) 2016," Modern Pathology, 2017.

[18] F. Grizzi, G. Celesti, G. Basso, and L. Laghi, "Tumor budding as a potential histopathological biomarker in colorectal cancer: Hype or hope?," World Journal of Gastroenterology: WJG, vol. 18, p. 6532, 2012.

[19] R. L. Siegel, K. D. Miller, S. A. Fedewa, D. J. Ahnen, R. G. Meester, A. Barzi, et al., "Colorectal cancer statistics, 2017," CA: a cancer journal for clinicians, vol. 67, pp. 177-193, 2017.

[20] V. H. Koelzer, N. Assarzadegan, H. Dawson, B. Mitrovic, A. Grin, D. E. Messenger, et al., "Cytokeratin-based assessment of tumour budding in colorectal cancer: Analysis in stage II patients and prospective diagnostic experience," The Journal of Pathology: Clinical Research.

[21] G. Rieger, V. H. Koelzer, H. E. Dawson, M. D. Berger, M. Hädrich, D. Inderbitzin, et al., "Comprehensive assessment of tumour budding by cytokeratin staining in colorectal cancer," Histopathology, vol. 70, pp. 1044-1051, 2017.

[22] A. Gordon, G. Glazko, X. Qiu, and A. Yakovlev, "Control of the mean number of false discoveries, Bonferroni and stability of multiple testing," The Annals of Applied Statistics, pp. 179-190, 2007.

[23] E. L. Korn and B. Freidlin, "A note on controlling the number of false positives," Biometrics, vol. 64, pp. 227-231, 2008.

[24] R. L. Siegel et al., "Colorectal cancer statistics, 2021," CA: a cancer journal for clinicians, 2021.

[25] V. H. Koelzer et al., "Tumor budding in colorectal cancer revisited: results of a multicenter interobserver study," Virchows Archiv, vol. 466, no. 5, pp. 485-493, 2015.

[26] K. Kai et al., "Cytokeratin immunohistochemistry improves interobserver variability between unskilled pathologists in the evaluation of tumor budding in T1 colorectal cancer," Pathology international, vol. 66, no. 2, pp. 75-82, 2016.

[27] G. Rieger et al., "Comprehensive assessment of tumour budding by cytokeratin staining in colorectal cancer," Histopathology, vol. 70, no. 7, pp. 1044-1051, 2017.

[28] A. Lugli et al., "Recommendations for reporting tumor budding in colorectal cancer based on the International Tumor Budding Consensus Conference (ITBCC) 2016," Modern Pathology, vol. 30, no. 9, p. 1299, 2017.

[29] Z. Liu et al., "Swin transformer: Hierarchical vision transformer using shifted windows," arXiv preprint arXiv: 2103.14030, 2021.

[30] A. Dosovitskiy et al., "An image is worth 16×16 words: Transformers for image recognition at scale," arXiv preprint arXiv: 2010.11929, 2020.

[31] A. Vaswani et al., "Attention is all you need," pp. 5998-6008.

[32] D. Mattes, D. R. Haynor, H. Vesselle, T. K. Lewellyn, and W. Eubank, "Nonrigid multimodality image registration," in Medical Imaging 2001: Image Processing, 2001, vol. 4322, pp. 1609-1620: International Society for Optics and Photonics.

[33] S. Rahunathan, D. Stredney, P. Schmalbrock, and B. D. Clymer, "Image registration using rigid registration and maximization of mutual information."

[34] M. Styner, C. Brechbuhler, G. Szckely, and G. Gerig, "Parametric estimate of intensity inhomogeneities applied to MRI," IEEE transactions on medical imaging, vol. 19, no. 3, pp. 153-165, 2000.

[35] M. K. Khan Niazi, M. M. Yearsley, X. Zhou, W. L. Frankel, and M. N. Gurcan, "Perceptual clustering for automatic hotspot detection from Ki-67-stained neuroendocrine tumour images," Journal of microscopy, vol. 256, no. 3, pp. 213-225, 2014.

[36] S. Graham et al., "Hover-net: Simultaneous segmentation and classification of nuclei in multi-tissue histology images," Medical Image Analysis, vol. 58, p. 101563, 2019.

[37] L.-C. Chen, G. Papandreou, F. Schroff, and H. Adam, "Rethinking atrous convolution for semantic image segmentation," arXiv preprint arXiv: 1706.05587, 2017.

[38] P. D. Caie, A. K. Turnbull, S. M. Farrington, A. Oniscu, and D. J. Harrison, "Quantification of tumour budding, lymphatic vessel density and invasion through image analysis in colorectal cancer," Journal of translational medicine, vol. 12, no. 1, p. 156, 2014.

[39] N. J. Pedersen et al., "Construction of a pathological risk model of occult lymph node metastases for prognostication by semi-automated image analysis of tumor budding in early-stage oral squamous cell carcinoma," Oncotarget, vol. 8, no. 11, p. 18227, 2017.

[40] C.-A. Weis et al., "Automatic evaluation of tumor budding in immunohistochemically stained colorectal carcinomas and correlation to clinical outcome," Diagnostic pathology, vol. 13, no. 1, p. 64, 2018.

[41] R. K. Jepsen et al., "Digital image analysis of pan-cytokeratin stained tumor slides for evaluation of tumor budding in pT1/pT2 colorectal cancer: Results of a feasibility study," Pathology-Research and Practice, vol. 214, no. 9, pp. 1273-1281, 2018.

[42] N. Brieu, C. G. Gavriel, I. P. Nearchou, D. J. Harrison, G. Schmidt, and P. D. Caie, "Automated tumour budding quantification by machine learning augments TNM staging in muscle-invasive bladder cancer prognosis," Scientific reports, vol. 9, no. 1, p. 5174, 2019.

[43] I. P. Nearchou, K. Lillard, C. G. Gavriel, H. Ueno, D. J. Harrison, and P. D. Caie, "Automated Analysis of Lymphocytic Infiltration, Tumor Budding, and Their Spatial Relationship Improves Prognostic Accuracy in Colorectal Cancer," Cancer immunology research, vol. 7, no. 4, pp. 609-620, 2019.

The invention claimed is:

1. A method for identifying tumor buds in an image of a hematoxylin & eosin (H&E) stained section of a tumor, the method comprising:

generating a ground truth of H&E stained slides having identified regions of tumor buds and/or identified regions that are not tumor buds;

training an artificial intelligence (AI) algorithm using the dataset of H&E stained slides, wherein the AI algorithm comprises a swin transformer; and analyzing the image of the H&E stained section of the tumor using the trained AI algorithm to determine a presence or absence of tumor buds on the H&E stained slide.

2. The method of claim 1, wherein the ground truth of H&E stained slides having identified regions of tumor buds and/or identified regions that are not tumor buds are generated by:

registering adjacent AE1/3 and H&E in order to provide a reliable ground truth for tumor regions and tumor budding;

utilizing one or more swin transformers to segment a malignant tumor region on one or more H&E images; and verifying the segmented malignant tumor regions found by the one or more swin transformers on the one or more H&E images, wherein a series of automatic post-processing steps transfer small positive regions identified on AE1/3 (potential tumor buds) onto registered H&E, where they are filtered by number of nuclei to determine if they comprise a tumor bud.

3. A method for identifying tumor buds in an image of a hematoxylin & eosin (H&E) stained section of a tumor, the method comprising:

generating a ground truth of H&E stained slides having identified regions of tumor buds and/or identified regions that are not tumor buds;

training an artificial intelligence (AI) algorithm using the dataset of H&E stained slides, wherein the AI algorithm further comprises a weakly-supervised machine learning method where labels are assigned to collections (called bags) rather than individual examples (called instances); and analyzing the image of the H&E stained section of the tumor using the trained AI algorithm to determine a presence or absence of tumor buds on the H&E stained slide, wherein the weakly-supervised machine learning method comprises attention-based (AB) multiple-instance learning (MIL), wherein one or more of the bags are identified from the H&E stained slide image, each bag comprising tessellated whole-slide images (WSIs), in which each instance is a small unannotated image sampled from the WSI, and wherein an attention-based pooling mechanism automatically learns to weight embedded instances into a bag-level feature vector dynamically, wherein a weight is automatically computed for each embedded instance, then a weighted sum combines them into a single, bag-level instance, corresponding to a slide-level embedding, and classification or regression is then performed on this bag-level embedding.

4. The method of claim 3, wherein the attention-based pooling mechanism comprises a two-layer fully connected neural network that passes each instance embedding ($h_k$) through two parallel layers of the network (V,U), applies a tanh and sigmoid activation function to the respective results, dots the results, then passes the fused activation through another layer ($w^T$), which maps the vector into a single value, its attention weight ($a_k$), wherein $$\frac{\exp\{w^T \tanh(Vh_k^T) \cdot sigm(Uh_k^T)\}}{\sum_{j=1}^{K} \exp\{w^T \tanh(Vh_j^T) \cdot sigm(Uh_k^T)\}}.$$

5. The method of claim 4, wherein a weighted sum of each embedded instance and its attention weight yields a bag-level instance (z), where $$z = \sum_{k=1}^{K} a_k h_k.$$

6. The method of claim 4, wherein parameters (V, U, w) for the two-layer neural network are automatically learned through model training.

7. The method of claim 6, wherein the model training comprises using SqueezeNet pretrained on ImageNet as a feature extractor to generate instance embeddings ($h_k$).

8. The method of claim 3, wherein each bag comprises a 512×512 pixel section of the WSI, and each instance comprises a 96×96 pixel section of each bag.

9. The method of claim 3, wherein a tumor budding label is assigned to each bag.

10. A method for identifying tumor buds in an image of a hematoxylin & eosin (H&E) stained section of a tumor, the method comprising:

generating a ground truth of H&E stained slides having identified regions of tumor buds and/or identified regions that are not tumor buds;

training an artificial intelligence (AI) algorithm using the dataset of H&E stained slides, wherein the AI algorithm comprises a weakly-supervised machine learning method where labels are assigned to bags comprising tessellated whole-slide images (WSIs) rather than instances comprising a small unannotated image sampled from the WSI; and analyzing the image of the H&E stained section of the tumor using the trained AI algorithm to determine a presence or absence of tumor buds on the H&E stained slide, wherein a tumor budding label is assigned to each bag.

11. The method of claim 10, wherein the weakly-supervised machine learning method comprises attention-based (AB) multiple-instance learning (MIL).

12. A method for identifying tumor buds in an image of a hematoxylin & eosin (H&E) stained section of a tumor, the method comprising:

generating a ground truth of H&E stained slides having identified regions of tumor buds and/or identified regions that are not tumor buds;

training an artificial intelligence (AI) algorithm using the dataset of H&E stained slides, wherein the AI algorithm comprises a weakly-supervised machine learning method where labels are assigned to bags comprising tessellated whole-slide images (WSIs) rather than instances comprising a small unannotated image sampled from the WSI; and analyzing the image of the H&E stained section of the tumor using the trained AI algorithm to determine a presence or absence of tumor buds on the H&E stained slide, wherein an attention-based pooling mechanism automatically learns to weight embedded instances into a bag-level feature vector dynamically, wherein a weight is automatically computed for each embedded instance, then a weighted sum combines them into a single, bag-level instance, corresponding to a slide-level embedding, and classification or regression is then performed on this bag-level embedding.

13. The method of claim 12, wherein the attention-based pooling mechanism comprises a two-layer fully connected neural network that passes each instance embedding (hk) through two parallel layers of the network (V,U), applies a tanh and sigmoid activation function to the respective results, dots the results, then passes the fused activation through another layer ($w^T$), which maps the vector into a single value, its attention weight ($a_k$), wherein $$\frac{\exp\{w^T \tanh(Vh_k^T) \cdot sigm(Uh_k^T)\}}{\sum_{j=1}^{K} \exp\{w^T \tanh(Vh_j^T) \cdot sigm(Uh_k^T)\}}.$$

14. The method of claim 13, wherein a weighted sum of each embedded instance and its attention weight yields a bag-level instance (z), where $$z = \sum_{k=1}^{K} a_k h_k.$$

15. The method of claim 13-, wherein parameters (V, U, w) for the two-layer neural network are automatically learned through model training.

16. The method of claim 15, wherein the model training comprises using SqueezeNet pretrained on ImageNet as a feature extractor to generate instance embeddings (hk).

17. A method for identifying tumor buds in an image of a hematoxylin & eosin (H&E) stained section of a tumor, the method comprising:

generating a ground truth of H&E stained slides having identified regions of tumor buds and/or identified regions that are not tumor buds;

training an artificial intelligence (AI) algorithm using the dataset of H&E stained slides, wherein the AI algorithm comprises a weakly-supervised machine learning method where labels are assigned to bags comprising tessellated whole-slide images (WSIs) rather than instances comprising a small unannotated image sampled from the WSI; and analyzing the image of the H&E stained section of the tumor using the trained AI algorithm to determine a presence or absence of tumor buds on the H&E stained slide, wherein each bag comprises a 512×512 pixel section of the WSI, and each instance comprises a 96×96 pixel section of each bag.

* * * * *